(12) United States Patent
Lee et al.

(10) Patent No.: US 10,495,560 B2
(45) Date of Patent: Dec. 3, 2019

(54) METHOD OF SCREENING DRUGS

(71) Applicant: KOREA RESEARCH INSTITUTE OF STANDARDS AND SCIENCE, Daejeon (KR)

(72) Inventors: Ri Mi Lee, Daejeon (KR); Dong Hyun Jo, Seoul (KR); Jeong Hun Kim, Seoul (KR); Tae Geol Lee, Daejeon (KR)

(73) Assignee: KOREA RESEARCH INSTITUTE OF STANDARDS AND SCIENCE, Daejeon (KR)

(*) Notice: Subject to any disclaimer, the term of this patent is extended or adjusted under 35 U.S.C. 154(b) by 869 days.

(21) Appl. No.: 14/615,596

(22) Filed: Feb. 6, 2015

(65) Prior Publication Data
US 2016/0231222 A1   Aug. 11, 2016

(51) Int. Cl.
*G01N 15/08* (2006.01)
(52) U.S. Cl.
CPC ..... *G01N 15/08* (2013.01); *G01N 2015/0853* (2013.01)
(58) Field of Classification Search
CPC .......................... G01N 15/08; G01N 33/5064
USPC .......................................................... 435/29
See application file for complete search history.

(56) References Cited

U.S. PATENT DOCUMENTS 5,187,096 A * 2/1993 Giaever ............. G01N 33/4836
                                                      204/403.01
2007/0259331 A1* 11/2007 Abeygunaratne .... G01N 27/447
                                                      435/4

FOREIGN PATENT DOCUMENTS

KR   20100112818   10/2010

OTHER PUBLICATIONS

KR20100112818, English Machine Translation of Description, pp. 1-12.*

* cited by examiner

*Primary Examiner* — Jennifer M. H. Tichy
(74) *Attorney, Agent, or Firm* — Cantor Colburn LLP

(57) ABSTRACT

Provided is a method for screening drugs, more particularly, a method for screening drugs by measuring capacitance of an endothelial cell layer at a frequency region of 100 Hz to 5 kHz to screen a drug affecting paracellular permeability of the endothelial cell layer or a drug penetrating through a paracellular path.

6 Claims, 13 Drawing Sheets
(12 of 13 Drawing Sheet(s) Filed in Color)

METHOD OF SCREENING DRUGS

TECHNICAL FIELD

The following disclosure relates to a method for screening drugs, and more particularly, to a method for screening drugs capable of screening drugs affecting paracellular permeability of an endothelial cell layer by measuring frequency-dependent capacitance of the endothelial cell layer.

BACKGROUND

Most of the endothelium in the body is continuous endothelium (endothelial layer), and continuous endothelium is observed in the blood-brain barrier, diaphragm, muscular tissue of the duodenum, fat, heart, papillary microvascular system, large vessel, lung, mesentery, nerve, blood-retina barrier, skeletal muscle, testis, and in or in the vicinity of another tissue or organ in the body. The continuous endothelium forms a semi-permeable membrane forming a barrier between tissue or organs contacting each other and permitting permeation of water, ions, a small molecule, a macromolecule, and cells by a regulated scheme. Various diseases may be caused by abnormal permeation of materials in the endothelial layer. Alternatively, as the disease progresses, abnormal permeation of materials in the endothelial layer may be generated. As an example, it was known that abnormal permeation in the brain microvascular endothelial cell layer is closely associated with initiation and progression of brain diseases such as Alzheimer's disease, stroke, and multiple sclerosis.

Further, in the case of injecting a drug into a specific tissue in the human body in order to treat a disease, endothelial barrier permeability of the drug should be secured as well as the development of the drug itself. As an example, in the case of the brain microvascular endothelial cell layer, there is almost no caveolae, and the binding between endothelial cells is strong (tight junction), such that permeation of drugs having a large molecular weight such as a protein is substantially impossible.

Therefore, researches into permeability of a material in the endothelial cell layer according to expression or progression of diseases, permeability of drugs in the endothelial cell layer, drugs capable of adjusting permeability of drugs in the endothelial cell layer, drugs capable of recovering an abnormal endothelial cell layer, and the like, should be conducted in medical and pharmaceutical fields. However, substantially, a method capable of measuring permeability of the endothelial cell layer in vitro and measuring and evaluating a change against external stimulation including drugs has been barely suggested.

Meanwhile, dielectric spectroscopy, which is to apply an alternating current (AC) electric field to cells to thereby measure specific dielectric responses according to interfacial polarization patterns, is a method applied in order to observe various cellular functions such as viability or death of a single cell, anabolism and differentiation of cells by endomitosis, cell stress, and the like.

The dielectric spectroscopy may observe living cells in vitro under an environment similar to that in the human body based on electric response to AC stimulation and analyze the status of the living cells. In addition, there is no need for pretreatment of a sample according to a complicated protocol, an expensive apparatus, and drug in the dielectric spectroscopy, etc., such that the dielectric spectroscopy is a significantly useful method in a commercial view.

The present applicant found that permeability of the endothelial cell layer may be precisely measured in vitro by using the dielectric spectroscopy, and a change in the permeability of the endothelial cell layer against external stimulation including drugs may be measured and evaluated, thereby completing the present invention.

SUMMARY

An embodiment of the present invention is directed to providing a method for screening drugs capable of screening drugs affecting permeability of an endothelial cell layer in vitro by using a simple sensor (apparatus).

More specifically, the embodiment of the present invention is directed to providing a method for screening drugs capable of simply and reproducibly screening drugs affecting permeability of an endothelial cell layer, such as a drug increasing permeability of an endothelial cell layer, a drug for treating an endothelial cell layer having abnormal permeability, or the like, with low cost.

Another embodiment of the present invention is directed to providing a method for evaluating integrity of an endothelial cell layer by testing permeability of the endothelial cell layer in vitro using a simple sensor (apparatus).

In one general aspect, a method for screening drugs is performed by measuring capacitance of an endothelial cell layer contacting a drug at a frequency region of 100 Hz to 5 kHz to screen a drug affecting paracellular permeability of the endothelial cell layer.

The method for screening drugs may include: a) stabilizing a cultured endothelial cell layer between two electrodes spaced apart from each other and facing each other; b) contacting the fixed endothelial cell layer with a drug; c) measuring capacitance of the endothelial cell layer contacting with the drug according to a time at a frequency of 100 Hz to 5 kHz to obtain a frequency-dependent capacitance value at each measurement time; and d) screening drugs affecting paracellular permeability of the endothelial cell layer based on the frequency-dependent capacitance value at each measurement time.

The method for screening drugs may further include, after step a), measuring capacitance of the fixed endothelial cell layer that does not contact drugs according to a time at a frequency of 100 Hz to 5 kHz to obtain a frequency-dependent reference capacitance value of the endothelial cell at each measurement time. In detail, the method for screening drugs may further include, after step a), measuring capacitance of the fixed endothelial cell layer at a frequency of 100 Hz to 5 kHz according to the time similarly in step c) to obtain the frequency-dependent reference capacitance value at each measurement time instead of performing step b).

Step d) may include comparing the frequency-dependent reference capacitance value at each measurement time with the frequency-dependent capacitance value at each measurement time obtained in step c) to screen drugs affecting paracellular permeability of the endothelial cell layer.

Step d) may include assigning the capacitance (log scale) to a y axis and the frequency (log scale) to an X axis and line-fitting the frequency-dependent reference capacitance values at each measurement time to obtain a reference alpha ($\alpha_{ref}$) value, which is a slope, assigning the capacitance (log scale) to a y axis and the frequency (log scale) to an X axis and line-fitting the frequency-dependent capacitance value at each measurement time obtained in step c) to obtain an alpha ($\alpha$) value, which is a slope, and comparing a measurement time-dependent alpha value and a measurement-time dependent reference alpha value with each other to screen drugs affecting paracellular permeability of the endothelial cell layer.

In the case in which an absolute value of an alpha value at a time point after 25 to 60 hours of contact with a drug is smaller than an absolute value of a reference alpha value, the drug may be screened as a drug increasing paracellular permeability.

Based on a drug contact time point, when a slope of the alpha value, which is a change in the time-dependent alpha value, has a different sign (+ or −) from that of a slope of the reference alpha value, which is a change in the time-dependent reference alpha value, the drug may be screened as a drug increasing paracellular permeability.

In the case in which a standardized capacitance value obtained by dividing a capacitance value at one frequency at a time point after 20 to 60 hours of contact with a drug by a capacitance value at a drug contact time point and the same frequency is smaller than a standardized reference capacitance value obtained by dividing a reference capacitance value at the same time point and the same frequency by a capacitance value at the drug contact time point and the same frequency, the drug may be screened as a drug increasing paracellular permeability of the endothelial cell layer.

Step d) may include: d1) assigning the capacitance value (log scale) to a y axis and the frequency (log scale) to an x axis and line-fitting the frequency-dependent capacitance value at each measurement time to obtain an alpha (a) value, which is a slope; and d) screening drugs affecting paracellular permeability of the endothelial cell layer based on the measurement time-dependent alpha value.

In step d2), in the case in which an absolute value of the time-dependent alpha value is continuously decreased for at least 3 to 5 hours based on the drug contact time point, the drug may be screened as a drug increasing paracellular permeability of the cell layer.

In step d2), in the case in which a standardized capacitance value obtained by dividing a capacitance value at one frequency selected from 100 Hz to 5 kHz at a time point after 10 to 30 hours of the drug contact time point by a capacitance value at the drug contact time point and the same frequency is continuously decreased for at least 5 hours or more, the drug may be screened as a drug increasing paracellular permeability of the cell layer.

One frequency may be 100 to 300 Hz.

Capacitance in step c) may be measured by applying an AC voltage of 5 to 15 mV to two electrodes.

The endothelial cell layer may be a vascular endothelial cell layer.

The vascular endothelial cell layer may be a brain microvascular endothelial cell layer.

Other features and aspects will be apparent from the following detailed description, the drawings, and the claims.

BRIEF DESCRIPTION OF THE DRAWINGS

The patent or application file contains at least one drawing executed in color. Copies of this patent or patent application publication with color drawing(s) will be provided by the office upon request and payment of the necessary fee.

DETAILED DESCRIPTION OF EMBODIMENTS

Figure 1A:
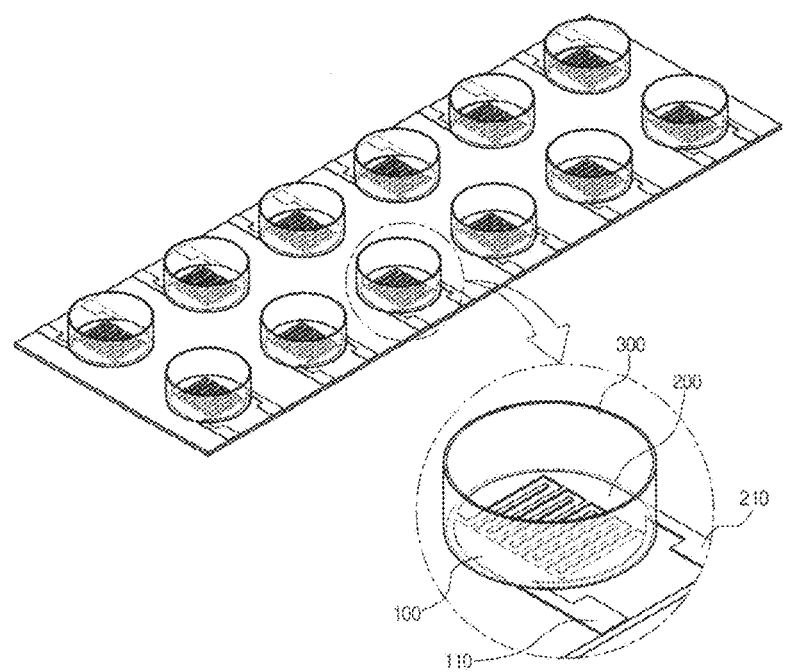
FIG. 1A and FIG. 1B are perspective views illustrating a structure of a capacitance sensor used in a method for screening drugs according to an exemplary embodiment of the present invention.

Hereinafter, a method for screening drugs according to the present invention will be described in detail. Here, technical terms and scientific terms used in the present specification have the general meaning understood by those skilled in the art to which the present invention pertains unless otherwise defined, and a description for the known function and configuration unnecessarily obscuring the present invention will be omitted in the following description and the accompanying drawings.

For basic researches including research into material permeability of an endothelial cell layer according to expression or progression of a disease, research into drug permeability of the endothelial cell layer, and the like, and development of a drug capable of adjusting permeability of a cell layer and a drug capable of recovering an abnormal endothelial cell layer, a method capable of measuring and evaluating paracellular permeability of the endothelial cell layer and paracellular permeability of the endothelial cell layer against external stimulation including drugs in vitro should be developed in advance.

The present applicant recognized the importance and conducted in-depth research into a method capable of precisely and reproducibly measuring the paracellular permeability of the endothelial cell layer in vitro over a long period of time. As a result of this research, it was found that capacitance may be changed in a frequency region of 100 Hz to 5 kHz according to relationship (structure) between cells instead of a single cell such as a degree of tight junction between cells forming a cell 'layer', a cell wall instead of an internal portion of the cell, a volume between cells, or the like, and capacitance in a frequency region of 100 Hz to 5 kHz directly reflects paracellular permeability of the endothelial cell layer.

The present applicant conducted in-depth research into the paracellular permeability of the endothelial cell layer against external stimulation including drugs based on the founding as described above, thereby confirming that a drug affecting paracellular permeability of the endothelial cell layer may be screened without highly professional knowledge by a simple and rapid method of only measuring capacitance of vascular endothelial cell layer contacting the drug at a frequency region of 100 Hz to 5 kHz.

The method for screening drugs according to the present invention is a method for screening drugs affecting paracellular permeability of the endothelial cell layer by measuring capacitance of the endothelial cell layer contacting the drugs at a frequency region of 100 Hz to 5 kHz.

According to the related art, only a shape of a single cell or changes in characteristics, differentiation, or the like, may be measured using dielectric spectroscopy. However, according to the present invention, it was found that permeability of a layer in which cells are organized instead of an individual cell, particularly, paracellular permeability may be measured and evaluated using the dielectric spectroscopy, and it was found that a change in paracellular permeability against external stimulation including drugs may also be measured and evaluated as described above.

The method for screening drugs according to the present invention may include: a) fixing a cultured endothelial cell layer between two electrodes spaced apart from each other and facing each other; b) contacting the fixed endothelial cell layer with a drug; c) measuring capacitance of the endothelial cell layer contacting the drug according to a time at a frequency of 100 Hz to 5 kHz to obtain a frequency-dependent capacitance value at each measurement time; and d) screening drugs affecting paracellular permeability of the endothelial cell layer based on the frequency-dependent capacitance value at each measurement time.

The term 'paracellular permeability' may mean movement of materials such as ions, molecules, liquids, and the like, through an endothelial cell junction, which is a portion between the endothelial cells of the endothelial cell layer.

The term 'endothelial cell layer' may mean a layer in which endothelial cells are organized. The organized cell layer may include a monolayer of the endothelial cells or a multilayer in which monolayers of the endothelial cells are stacked. The endothelial cell layer may include a vascular endothelial cell layer. The vascular endothelial cell layer may include a microvascular endothelial cell layer, capillary endothelial cell layer, or a neovascular endothelial cell layer.

Based on a body structure, 'endothelial cells' configuring the endothelial cell layer may be cells configuring endothelia found in the liver, the spleen, the bone marrow, the pancreas, the adrenal gland, the endocrine gland, the intestines, the brain, the diaphragm, muscle tissue of the duodenum, fat, the heart, the kidney, (papillary microvascular system, descending straight tubules), the great arteries, the lung, the mesentery, the nerve, the retina, the skeletal muscle, or the testicles. Here, in the case of the organ exposed to the outside such as the retina, the endothelia also include the meaning of epidermis.

The 'endothelial cells' may be directly extracted from the body or cell lines commercially sold on the market. In this case, the body may mean a body of animals including human.

Integrity of the endothelial cell layer significantly affects homeostasis and expression of a disease, and as an example of the endothelial cell layer through which permeation of drugs is difficult, the endothelial cell layer may include brain microvascular endothelial cell layer.

The term 'drug' may mean a biochemical material or drug for treating diseases, containing cell materials; genetic materials; metabolites of an organism; or organic materials affecting a biosynthesis process/transport process/or signaling process of an organism. That is, in the present invention, the drug is not limited to a material used in order to treat diseases occurring in animals including human beings, but the drug may include a material 'capable of being used' in order to 'prevent', 'diagnose', or 'treat' diseases occurring in animals including human beings, and may include a product caused by expression of disease or a biochemical material causing diseases.

Therefore, the 'drug' may include a candidate drug group; and/or drug group for treating diseases.

The 'candidate drug' group may include the above-mentioned biochemical material. In this case, the candidate drug group may include biochemical materials of which an influence affecting permeability of the endothelial cell layer is not clearly found. The influence is not clearly found, which means that an influence depending on an amount of the corresponding biochemical material in addition to an influence of the corresponding biochemical material itself on the permeability of the endothelial cell layer are not found. Further, the biochemical material of the candidate drug group may also include the case in which a degree of an influence of the corresponding material or a combination of the corresponding materials on the permeability of the endothelial cell layer is not clearly found.

According to the present invention, the drug capable of increasing permeability of the endothelial cell layer or healing an abnormal endothelial cell layer having excessive permeability as compared to a normal endothelial cell layer into an endothelial cell layer having normal permeability may be screened.

In addition, an amount of a drug for clinically obtaining the desired effect may be tested in vitro by repeatedly performing step b) and step d) to be described while changing an amount of the drug contacting the fixed endothelial cell layer. That is, a change in the paracellular permeability of the endothelial cell layer depending on the amount of the drug may also be evaluated.

As described above, in the present invention, as the drug includes the biochemical material containing the cell materials; the genetic materials; the metabolites of the organism; or the organic materials affecting the biosynthesis process/transport process/or signaling process of the organism, the present invention includes a method for screening biochemical materials affecting paracellular permeability of an endothelial cell layer by measuring capacitance of the endothelial cell layer contacting the drug at a frequency region of 100 Hz to 5 kHz.

The 'drug group for treating diseases' is not particularly limited, but may include a drug group for treating diseases caused by a malfunction in permeability of the endothelial cell layer or diseases causing a malfunction in permeability of the endothelial cell layer. In the case of contacting the drug group for treating the diseases caused by malfunction in permeability of the endothelial cell layer or causing malfunction in permeability of the endothelial cell layer with the endothelial cell layer, the method for screening drugs according to the present invention may also provide a clue for understanding disease treatment mechanism of the corresponding drug.

The diseases caused by malfunction in the permeability of the endothelial cell layer or causing malfunction in the permeability of the endothelial cell layer may include diseases caused by malfunction in the permeability of the vascular endothelial cell layer or causing malfunction in the permeability of the vascular endothelial cell layer.

Based on the vascular endothelial cell layer, specific examples of the 'diseases' in the 'drug group for treating diseases' may be selected from the group consisting of cerebrovascular disease (CVA), Alzheimer's disease (AD), vascular-related dementia, Creutzfeldt-Jakob disease (CJD), bovine spongiform encephalopathy (BSE), Parkinson's disease (PD), multiple sclerosis (MS), amyotrophic lateral sclerosis (ALS) or Huntington's chorea, septic shock, arterial brain disorder, hypertension, diabetic microangiopathy, sleeping sickness, Whipple's disease, Duchenne muscular dystrophy (DMD), aspartylglucosaminuria, cholesterol ester storage disease, Wolman disease, cystinosis, Danon disease, Faby's disease, Farber liposarcoma, Farber's disease, fucosidosis, galactosialidosis types I/II, Gaucher disease types I/II/III, Gaucher disease, globoid cell leukodystrophy, Krabbe's disease, glycogen storage disease type II, Pompe disease, GM1-gangliosidosis types I/II/III, GM2-gangliosidosis type I, Tay-Sachs disease, GM2-gangliosidosis type II, Sandhoff disease, alpha-mannosidosis types I/II, mannosidosis, metachromatic leucodystrophy, mucolipidosis type I, sialidosis types I/II, mucolipidosis types II/III, 1-cell disease, mucolipidosis type IIIC, pseudo-Hurler polydystrophy, mucopolysaccharidosis type I, mucopolysaccharidosis type II, Hunter syndrome, mucopolysaccharidosis type IIIA, Sanfilippo syndrome, mucopolysaccharidosis type IIIB, mucopolysaccharidosis type IIIC, mucopolysaccharidosis type IIID, mucopolysaccharidosis type IVA, Morquio syndrome, mucopolysaccharidosis type IVB, mucopolysaccharidosis type VI, mucopolysaccharidosis type VII, Sly syndrome, mucopolysaccharidosis type IX, multiple sulphatase deficiency, neuronal ceroid lipofuscinosis, CLN1 Batten disease, Niemann-Pick disease types A/B, Niemann-Pick disease, Niemann-Pick disease type C1, Niemann-Pick disease type C2, pycnodysostosis, Schindler disease types VII, Schindler disease, sialic acid storage disease, (pre)eclampsia, depression, autism, anxiety attention deficit hyperactivity disorder (ADHD), neuropsychiatric systemic lupus erythematosus, bipolar disorder, schizophrenia, brain tumors, epilepsy, migraine, narcolepsy, insomnia, chronic fatigue syndrome, mountain sickness, encephalitis, meningitis, vascular tumors, proliferative vitreoretinopathy, rheumatoid arthritis, Crohn's disease, atherosclerosis, ovarian hyperstimulation, psoriasis, endometriosis associated with neovascularisation, restenosis subsequent to balloon angioplasty, scar tissue overproduction, peripheral vascular disease, inflammatory vasculitides, Raynaud's disease, Raynaud's phenomenon, aneurysms, arterial restenosis, thrombophlebitis, lymphangitis, lymphedema, wound healing and tissue repair, ischemia reperfusion injury, angina, myocardial infarctions, chronic heart conditions, heart failure such as congestive heart failure, age-related macular degeneration, and osteoporosis.

The drug for treating diseases may be a drug for treating the above-mentioned specific examples of the diseases. In this case, the drug for treating diseases may include commercialized drugs of which a treatment effect on the above-mentioned diseases was proven and/or drugs in development.

According to the present invention, drugs increasing or decreasing paracellular permeability of the endothelial cell layer may be screened by contacting the drugs belonging to the drug group for treating diseases with the fixed endothelial cell layer.

The drug contacting the fixed endothelial cell layer may be a single drug or a combination of two or more drugs. In the case of contacting two or more drugs with the fixed endothelial cell layer, an influence by interactions between the drugs on permeability of the endothelial cell layer may be evaluated, and the combination of two or more drugs may be screened as the combination itself. In this case, the combination of the drugs may be a combination of two or more drugs selected from the above-mentioned candidate drug group and drug group for treating diseases.

The 'drug' includes a biochemical material or a carrier (pharmaceutically acceptable carrier) which the biochemical material is bound to or supported on. The carrier may be an organic, inorganic, or organic-inorganic carrier. Here, the inorganic carrier may include inorganic nanoparticles, wherein the inorganic nanoparticles may include metal nanoparticles, metal oxide nanoparticles, and metal nitride nanoparticles.

Although drugs capable of being used in the present invention are described in detail in order to assist in the understanding of the present invention, since the present invention relates to a method for screening arbitrary drugs (including the combination of two or more drugs) of which an effect is clearly identified or is not clearly identified, the present invention is not limited to a material or a content of the drug.

That is, since the method for screening drugs according to the present invention is a method for screening drugs by determining an influence of a drug of which an effect has already been known or a drug of which an effect is not clearly known on the paracellular permeability of the endothelial cell layer based on time and frequency-dependent capacitance values, any drug of which an influence on the paracellular permeability of the endothelial cell is desired to be known may become a target of screening of the present invention.

The term 'cultured endothelial cells' may mean endothelial cells proliferated by a culture material generally used to culture animal cells. As a specific and non-restrictive example, the culture materials may include a medium, serum, and antibiotics that are generally used to culture animal cells. The medium may be a general animal cell medium containing amino acids, vitamins, inorganic salts, glucose, lipids, and the like. As the animal cell medium, a product commercially sold on the market in order to culture animal cells may be used. As a specific example of the commercialized animal cell medium, there is Dulbecco's modified eagle's medium (DMEM), Rosewell Park Memorial Institute (RPMI), 1640 Medium MEM (Minimum Essential Medium), or the like. As an example of generally used serum, there is fetal bovine serum (FBS), or the like, and as an example of generally used antibiotics, there are penicillin, streptomycin, and the like. Contents of serum and antibiotics in the culture materials may be contents used to culture general animal cells. As an example, the culture material may include 5 to 15 vol % of serum and 0.5 to 1.5 vol % of antibiotics. In this case, the culture material may further include a general additive known to be useful to maintain animal cells to be alive in a normal state and proliferate animal cells in the normal state. In addition, a temperature and atmosphere may be adjusted so as to be suitable for characteristics of cells to be cultured at the time of culture. As an example, the culture may be performed at a temperature similar to a body temperature (36.5 to 37.5° C.) under atmosphere in which carbon dioxide and air are mixed. A culturing temperature and atmosphere may be adjusted using an incubator for culturing cells. The culturing method, the culturing solution, and the like, of the endothelial cell are described in detail in order to assist in the clear understanding of the present invention, but the culturing method of animal cells is known to those skilled in medical, pharmacological, and biological fields. Therefore, the present invention is not limited to the above-mentioned culture conditions or method.

The cultured endothelial cell may be seeded and stabilized (fixed) to a sensor capable of measuring capacitance together with a culture material. In this case, the culture material used at the time of stabilization may include a medium, serum, and antibiotics generally used to culture animal cells similarly to the culturing of the endothelial cells as described above.

Figure 1B:
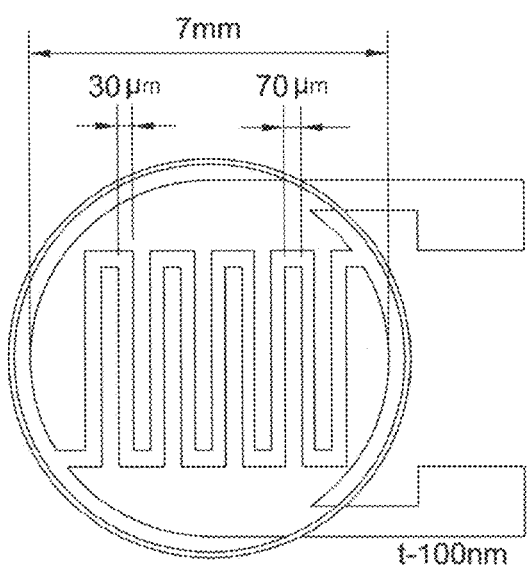

As illustrated in an example of FIG. 1, a capacitance sensor capable of measuring capacitance may include a substrate; two electrodes 100 and 200 spaced apart from each other and facing each other on the substrate; and connection terminals 110 and 210 extended from the electrodes, respectively, so as to electrically connect the electrodes to external power source. In addition, the capacitance sensor may further include a well 300 adhered so as to enclose a measurement region corresponding to a region at which two electrodes 100 and 200 spaced apart from each other and facing each other are positioned. As the well, a commercialized product generally used to culture animal cells may be purchased and adhered so as to enclose the measurement region to thereby be used.

As the substrate, any substrate may be used as long as it is an electric non-conductor and does not biochemically react. As an example, the substrate may be a glass substrate, but the present invention is not limited thereto.

A gap between first and second electrodes, which are two electrodes spaced apart from each other and facing each other, is a space into which the cultured endothelial cells are inserted to thereby be adhered (fixed) thereto while forming a monolayer. In more detail, since the gap between the first and second electrodes is a region into which the seeded endothelial cells are inserted and stabilized and in which an endothelial cell monolayer is formed, a spaced distance between the first and second electrodes may be suitably adjusted in consideration of a size of the corresponding endothelial cell.

As a specific example, an interval (size of the gap) between the first and second electrodes may be 1 to 3 times, more specifically, 1 to 2 times based on a diameter D1 of the endothelial cell. In this case, the diameter of the endothelial cell may mean an average diameter of the corresponding endothelial cells in a living state. As a specific and non-restrictive example, in the case in which the endothelial cells are brain microvascular endothelial cells, the interval between the first and second electrodes may be 20 to 40 μm. A thickness (height) of the electrodes is not particularly limited, but may be several ten nm to several μm more or less in view of stably collecting electric signals.

As electrode materials of the first and second electrodes, any material may be used as long as it has electric conductivity and is biochemically stable. As an example, the first and second electrodes may be each independently made of gold, platinum, or a conductive polymer, but the present invention is not limited thereto.

Shapes of the first and second electrodes are not particularly limited, but it is preferable that the first and second electrodes have shapes capable of increasing a contact area between the electrode and the endothelial cell layer and an amount of endothelial cell layers to be measured in order to improve sensitivity, accuracy, and reproducibility of measurement. In this regard, as illustrated in the example of FIG. 1, the first and second electrodes may have structures interdigitated with each other.

In order to prevent the endothelial cells positioned on the first and second electrodes from being attached to the electrodes and prevent generation of noise by the endothelial cells positioned on the first and second electrodes, an insulation layer may be positioned on the first and second electrodes. That is, except for side surfaces of the first and second electrodes facing each other, the other surfaces of the electrodes may be coated with the insulation layer. The insulation layer may be made of a material that is biochemically stable and non-conductive. As a non-restrictive example, the insulation layer may be made of polymethyl methacrylate (PMMA), silicon oxide, or the like.

In this case, in order to improve efficiency, when two electrodes spaced apart from each other and facing each other, connection terminals connected to two electrodes, respectively, and a well attached so as to enclose the region in which two electrodes spaced apart from each other and facing each other are formed are considered as a single unit, two or more units may be formed to be spaced part from each other on a single substrate. In this case, the endothelial cell layer may contact drugs equal to or different from each other in each unit.

The fixing (stabilizing) of the cultured endothelial cell layer between two electrodes means that the endothelial cells are fixed to the substrate simultaneously with stably forming a monolayer while filling the space between two electrodes by seeding the cultured endothelial cells in the gap corresponding to the region between at least two electrodes and then culturing the seeded endothelial cells for a predetermined time.

At the time of seeding, the seeding may be performed so that a lower portion of the well is entirely covered by the endothelial cells based on an area of the lower portion of the well in which two electrodes spaced apart from each other and facing each other are positioned. That is, at the time of seeding, the endothelial cells may be seeded so that a coverage becomes at least 95% or more, substantially 100% based on the coverage, which is a ratio (Ac/Ao*100%) of an area Ac of a lower portion of the well covered by the cultured endothelial cells to the area Ao of the lower portion of the well. Substantially, as the endothelial cells are seeded so that the lower portion of the well is entirely covered by the endothelial cells and then the seeded endothelial cells are stabilized through secondary culture, a deviation of the endothelial cell layer (monolayer) to be measured depending on the well may be prevented, and reproducibility and reliability of measurement results may be improved.

After seeding, culturing (secondary culturing) in order to allow the endothelial cells inserted into the gap between two electrodes to be fixed while forming a stable layer (monolayer) may be performed. At the time of secondary culturing, the above-mentioned culture material in the previous culturing of the endothelial cell may be supplied to the well together with the endothelial cells. The secondary culturing may be performed using an incubator for culturing cells at the above-mentioned temperature and atmosphere in the previous culturing of the endothelial cell. The secondary culturing is performed for a time for which a stable endothelial cell monolayer is formed and fixed. As an example, the secondary culturing may be performed for 12 to 36 hours.

As described above, a) the fixing of the cultured endothelial cell layer between two electrodes spaced apart from each other and facing each other may include a1) culturing endothelial cells; a2) seeding the cultured endothelial cells in a measurement region of a sensor including two electrodes spaced apart from each other and facing each other on a substrate and a well enclosing the measurement region corresponding to a region in which two electrodes are formed, injecting a culture material into the well, and culturing (secondarily culturing) so that the cultured endothelial cells are inserted into a gap between two electrodes to thereby be fixed thereto while forming a monolayer.

Thereafter, b) the contacting of the fixed endothelial cell layer with drugs may be performed. Step b) may be performed by a medium exchange method of exchanging the culture material supplied to the endothelial cell for secondary culturing with a culture material containing a drug (hereinafter, drug containing medium). In detail, step b) may include: removing the culture material injected into the well in step a2) and injecting the drug containing medium into the well. Alternatively, the drug may be independently injected into the culture material supplied to the endothelial cells for secondary culturing. In detail, step b) may include: injecting the drug into the well.

It is preferable that a contact with the drug is performed by medium exchange. The reason is that in order to precisely detect a change in the endothelial cell layer due to the contact with the drug after the endothelial cell layers are stabilized, it is preferable that the culture material used for stabilization and the culture material used at the time of contact with the drug are different. That is, the culture material containing serum, which is a growth factor, is injected for fixation (stabilization), but in the contacting of the fixed endothelial cell layer with drugs, it is preferable to use a culture material that does not contain this growth factor.

As a specific example, the culture material used at the time of secondary culturing for fixation (stabilization) may include a medium, serum, and antibiotics that are generally used to culture animal cells. Thereafter, the exchanged drug containing culture material may include the drug, the medium, and antibiotics that are generally used to culture animal cells, but may not contain growth factors including serum.

A time point at which the endothelial cell layer contacts the drug may be defined as a measurement initiation time point (t=0), and time-dependent capacitance of the endothelial cell layer may be measured at a frequency region of 100 Hz to 5 kHz in step c).

That is, a time point at which the medium is exchanged or the drug is injected is defined as the measurement initiation time point (t=0), and a frequency-dependent capacitance value at each measurement time may be obtained by measuring capacitance of the endothelial cell layer contacting the drug according to time at a frequency of 100 Hz to 5 kHz.

A suitable frequency interval scanning or sweeping the frequency region of 100 Hz to 5 kHz is a frequency interval at which there is no structural change in the endothelial cell layer while capacitance is measured, and accordingly, the frequency-dependent capacitance value may be obtained from the endothelial cell layer in the same state. In this case, it is preferable that the frequency-dependent capacitance value includes capacitance values respectively measured by at least two frequencies, that is, a first frequency corresponding to a frequency of 100 to 300 Hz and a second frequency corresponding to a frequency of 1 to 5 kHz.

A total measurement time is not particularly limited as long as the endothelial cell layer fixed between the electrodes may be maintained in a living state when a time point at which the endothelial cell layer contacts the drug is defined as the measurement initiation time point. However, as described above, as the endothelial cells cultured so as to cover substantially 100% are seeded and stabilized, the total measurement time may be shortened. As a specific example, the total measurement time may be 3 to 5 days, more specifically, 3 to 4 days.

In this case, when the time point at which the endothelial cell layer contacts the drug is defined as the measurement initiation time point, measurement may be performed for at least 20 hours, specifically at least 30 hours, and more specifically 45 hours or more. An interval of the measurement time for measuring capacitance may be 5 minutes to 1 hour.

In order to obtain time-dependent capacitance value at each frequency (measurement time-dependent and frequency-dependent capacitance values), an AC voltage of 5 to 15 mV may be applied to the first and second electrodes. The AC voltage of 5 to 15 mA is a range capable of obtaining a reliable capacitance value without having a negative influence on cells.

Capacitance may be calculated by measuring dielectric constants at each time and each frequency using an impedance analyzer connected to the first and second electrodes and using an area of the pre-designed electrode (an area of a surface contacting the endothelial cell layer) and an interval between the electrodes.

In this case, after the above-mentioned fixation (stabilization) is performed and before capacitance is measured, verifying whether or not the endothelial cell monolayer fixed between two electrodes is normal may be further performed. In detail, the verifying, which is a process of verifying whether or not the endothelial cell monolayer in a normal state is fixed between two electrodes, may be further performed. This verification may be performed by performing medium exchange using a reference medium that does not contain the drug and serum (but may contain antibiotics) after the above-mentioned stabilization is performed and measuring time-dependent capacitance of the stabilized endothelial cell layer. In the case in which capacitance of the stabilized endothelial cell layer is not significantly changed according to time but maintains a constant value, it may be judged that the endothelial cell layer in the normal state is fixed between two electrodes.

After obtaining frequency-dependent capacitance value at each measurement time, d) the screening of drugs affecting paracellular permeability of the endothelial cell layer based on the frequency-dependent capacitance value at each measurement time may be performed.

The screening may be performed by comparing a frequency-dependent capacitance value of an ab-initio endothelial cell layer fixed between the electrodes at each measurement time (equal to each measurement time in step c)) with a frequency-dependent capacitance value at each measurement time obtained in step c).

That is, in order to screen drugs affecting paracellular permeability of the endothelial cell layer based on the frequency-dependent capacitance value of the ab-initio endothelial cell layer at each measurement time, obtaining a frequency-dependent reference capacitance value of the ab-initio endothelial cell layer at each measurement time may be further performed.

In this case, the ab-initio endothelial cell layer may mean an endothelial cell layer in a state in which the endothelial cell layer does not contact drug and is fixed between the electrodes. At the time of obtaining the reference capacitance value, environments are the same as the environments (culture material, temperature, atmosphere, and the like) to which the endothelial cell layer is exposed at the time of measuring the capacitance in step c), and measurement may be performed under the same conditions as the measurement conditions (measurement time, applied AC voltage, AC frequency, and the like) in step c) except for drugs.

In detail, after step a), in the obtaining of the reference capacitance value, the frequency-dependent reference capacitance value at each measurement time may be obtained by measuring capacitance of the fixed endothelial cell layer at a frequency of 100 Hz to 5 kHz according to the time similarly in step c), instead of performing step b).

In this case, step d) may include: comparing the frequency-dependent reference capacitance value at each measurement time with the frequency-dependent capacitance value at each measurement time obtained in step c) to screen drugs affecting paracellular permeability of the endothelial cell layer. Here, in order to clearly distinguish terms so as not to confuse the frequency-dependent reference capacitance value at each measurement time with the frequency-dependent capacitance value at each measurement time in step c), the frequency-dependent capacitance value at each measurement time in step c) after contact with the drug may be referred to as a frequency-dependent test capacitance value at each measurement time.

That is, in the case in which the frequency-dependent capacitance value at each measurement time obtained in step c) (that is, the test capacitance value) is different from the frequency-dependent reference capacitance value at each measurement time so that a difference therebetween exceeds an experimental error range, or in the case in which change tendencies in the measurement time-dependent and/or frequency-dependent capacitance value of the test capacitance value and the reference capacitance value are different from each other, the drug may be screened as a drug affecting paracellular permeability, for example, a drug increasing or decreasing paracellular permeability of the cell layer, or the like. In this case, the change tendency may mean one or more factors selected from an increase, a decrease, maintenance, an increasing rate, and a decreasing rate of the frequency- or time-dependent capacitance value.

In detail, step d) may include: assigning the capacitance (log scale) to a y axis and the frequency (log scale) to an X axis and line-fitting the frequency-dependent reference capacitance value at each measurement time to obtain a reference alpha ($\alpha_{ref}$) value, which is a slope, assigning the capacitance (log scale) to a y axis and the frequency (log scale) to an X axis and line-fitting the frequency-dependent capacitance value (test capacitance value) at each measurement time obtained in step c) to obtain an alpha ($\alpha$) value (collectively referred to as a test alpha value), which is a slope, and comparing a measurement time-dependent alpha value and a measurement time-dependent reference alpha value to screen drugs affecting paracellular permeability of the endothelial cell layer. As an example, in the case in which a change tendency of the time-dependent alpha value (test alpha value) and a change tendency of the time-dependent reference alpha value are different, the drug may be screened as a drug affecting paracellular permeability. In this case, the change tendency of the alpha value may mean one or more factors selected from an increase, a decrease, maintenance, an increasing rate, and a decreasing rate of the time-dependent alpha value.

In one aspect using the alpha value, in the case in which an absolute value of the alpha value (test alpha value) at a time point after 25 to 60 hours of contact with a drug is smaller than an absolute value of the reference alpha value, the drug may be screened as a drug increasing paracellular permeability. Here, a time point at which the alpha value is compared may be adjusted according to a rate at which the drug acts on the endothelial cell layer and a response by the drug is exhibited, but the time point (25 to 60 hours) is a time point at which judgment may be made regardless of the kind of drugs.

In another aspect using the alpha value, based on a drug contact time point, the change in the time-dependent alpha value (test alpha value), that is, when the time-dependent alpha value is shown by assigning the time to the x axis and the alpha value to the y axis, in the case in which a slope of the alpha value (test alpha value) has a different sign (+ or −) from that of a slope of the reference alpha value, the drug may be screened as a drug increasing paracellular permeability. In this case, the different sign means that when the slope of the reference alpha value is a positive value, the slope of the alpha value is a negative value, or when the slope of the reference alpha value is a negative value, the slope of the alpha value is a positive value. Here, the slope of the alpha value based on the drug contact time point may mean an average slope in a section after at least 4 hours from the drug contact time point, specifically, 6 hours, and more specifically, up to 10 hours.

Independently of the screening using the above-mentioned alpha value, in step d), drugs affecting paracellular permeability of the endothelial cell layer may be screened by comparing a measurement time-dependent capacitance value at one frequency and a measurement time-dependent reference capacitance value at the same frequency with each other.

At the time of comparing the reference capacitance value and the test capacitance value as described above, the compared capacitance value may be standardized as a capacitance value measured at a specific time point. That is, when a capacitance value at one time point (t1) and one frequency (f1) is defined as C(f1, t1), and a capacitance value at a specific time point (t0) and one frequency (f1) is defined as C(f1, t0), a standardized capacitance value may be C(f1, t1)/C(f1, t0). At the time of comparing the standardized capacitance value, the reference capacitance value may also be standardized as a reference capacitance value at a specific time point and one frequency. Experimental errors generated by a fine difference in culture conditions between the cells and an inherent fine difference between measurement sensors depending on a manufacturing method may be excluded by the stabilization as described above. As an example of the specific time point for standardization, there is a time point at which stabilization is performed, a drug contact time point, a time point at which a predetermined time elapses after stabilization is initiated, or a time point at which a predetermined time elapses after contact with a drug. In this case, since the capacitance value at a specific time point and one frequency is a constant, the present invention is not limited by the time point used for standardization.

In the case in which the standardized capacitance value and the standardized reference capacitance value are different from each other so that a difference therebetween exceeds an experimental error range, or change tendencies in the time-dependent standardized capacitance values are different from each other, the drug may be screened as a drug affecting paracellular permeability of the endothelial cell layer, for example, a drug increasing or decreasing paracellular permeability of the endothelial cell layer, or the like. In this case, the change tendency may mean one or more factors selected from an increase, a decrease, maintenance, an increasing rate, and a decreasing rate of the time-dependent standardized capacitance value.

More specifically, in the case in which the standardized capacitance value obtained by dividing the measurement time-dependent capacitance value at one frequency by the capacitance value at the drug contact time point and the same frequency is smaller than the standardized reference capacitance value obtained by dividing the reference capacitance value at the same time point and the same frequency by the reference capacitance value at the drug contact time point and the same frequency, the drug may be screened as a drug increasing paracellular permeability of the endothelial cell layer.

The capacitance value at one frequency (and the reference capacitance value at one frequency) may be measured by a predetermined interval for at least 20 hours or more, specifically, 20 to 60 hours, and more specifically 30 to 60 hours. As described above, the time point at which the capacitance value at one frequency is compared may be adjusted according to the rate at which the drug acts on the endothelial cell layer and the response by the drug is exhibited, but the time point (20 to 60 hours, specifically, 30 to 60 hours, and more specifically 40 to 60 hours) is a time point at which judgment may be made regardless of the kind of drugs.

As a specific example, in the case in which a standardized capacitance value at one frequency and a time point after 30 to 60 hours based on the drug contact time point is 97% or less of a standardized reference capacitance value at the same frequency (that is, in the case in which the standardized capacitance value is smaller than the standardized reference capacitance value), the drug may be screened as a drug increasing paracellular permeability of the endothelial cell layer.

As another specific example, in the case in which a standardized capacitance value at one frequency and a time point after 40 to 60 hours based on the drug contact time point is 95% or less of a standardized reference capacitance value at the same frequency (that is, in the case in which the standardized capacitance value is smaller than the standardized reference capacitance value), the drug may be screened as a drug increasing paracellular permeability of the endothelial cell layer.

A change in paracellular permeability of the endothelial cell layer may be more significantly shown in an extremely low frequency region of 100 to 300 Hz. Therefore, at the time of comparing the capacitance values at a single frequency, the single frequency (one frequency) may be in a range of 100 to 300 Hz.

That is, in the case in which a standardized capacitance value obtained by dividing a capacitance value at one frequency at a time point after 20 to 60 hours of contact with a drug the capacitance value at the drug contact time point and the same frequency is smaller than a standardized reference capacitance value obtained by dividing the reference capacitance value at the same time point and the same frequency by the reference capacitance value at the drug contact time point and the same frequency, the drug may be screened as a drug increasing paracellular permeability of the endothelial cell layer.

Independently of the method for screening drugs by comparing the reference capacitance value with the capacitance value (test capacitance value) measured in step c), drugs may be screened based on frequency-dependent capacitance value at each measurement times measured in step c).

In detail, step d) may include: d1) assigning the capacitance value (log scale) to a y axis and the frequency (log scale) to an x axis and line-fitting the frequency-dependent capacitance value at each measurement time to obtain an alpha (a) value, which is a slope; and d) screening drugs affecting paracellular permeability of the endothelial cell layer based on the measurement time-dependent alpha value.

In more detail, in step d2), in the case in which the time-dependent alpha value is continuously decreased for at least 3 to 5 hours based on an absolute value of the alpha value and the drug contact time point, the drug may be screened as a drug increasing paracellular permeability of the cell layer.

Independently, step d) may include: screening drugs affecting paracellular permeability of the cell layer based on a standardized capacitance value obtained by dividing a measurement time-dependent capacitance value at one frequency selected from 100 Hz to 5 kHz by a capacitance value at the drug contact time point and the same frequency.

In detail, step d) may include screening drugs as a drug increasing paracellular permeability of the cell layer in the case in which the measurement time-dependent standardized capacitance value at one frequency is continuously decreased. In this case, the continuous decrease may mean that after 10 to 30 hours of the drug contact time point, the capacitance value is continuously decreased for at least 5 hours or more. In this case, one frequency may be 100 Hz to 300 Hz.

As described above, the method for screening drugs according to the present invention is based on a method capable of directly evaluating paracellular permeability of the endothelial cell layer by measuring capacitance of the endothelial cell layer at 100 Hz to 5 kHz. Therefore, the present invention includes a method for evaluating integrity of an endothelial cell layer.

The method for evaluating integrity of an endothelial cell layer according to the present invention includes: e) fixing a cultured endothelial cell layer between two electrodes spaced apart from each other and facing each other; and f) measuring capacitance value of the contacted endothelial cell layer according to time at a frequency of 100 Hz to 5 kHz to obtain a frequency-dependent capacitance value at each measurement time.

In this case, since a measurement method of capacitance, a sensor capable of being used at the time of measuring capacitance, culturing of the endothelial cell, a culture material, the kind of endothelial cell, the fixing (stabilizing) of the cultured endothelial cell between two electrodes, and the like, are equal or similar to those in step a) of the method for screening drugs as described above, the method for evaluating the integrity may be performed with reference to the above-mentioned description.

In addition, since measurement in step f) is also equal or similar to that in step c) of the method for screening drugs as described above, step f) may be performed with reference to the above-mentioned description.

However, it is preferable to exchange a culture material containing serum, which is a growth factor, with a culture material that does not contain a growth factor through medium exchange at the time of secondary culturing before measurement in step f). That is, the exchanged medium may contain a medium generally used to culture animal cells but not contain serum.

Thereafter, the method for evaluating integrity of an endothelial cell layer according to the present invention may further include: assigning capacitance (log scale) to a y axis and a frequency (log scale) to an x axis and line-fitting the frequency-dependent capacitance value at each measurement time obtained in step f) to obtain an alpha (a) value, which is a slope. That is, after obtaining the alpha value as described above, integrity of the endothelial cell layer may be evaluated based on the alpha value.

More specifically, in the case in which the alpha value is gradually decreased but increased again with the passage of time and the alpha value is lowest after 15 to 25 hours based on a time point at which the medium is exchanged with the culture material that does not contain the growth factor, the endothelial cell layer may be evaluated as an endothelial cell layer without defects.

Independently, the method for evaluating integrity of an endothelial cell layer according to the present invention may further include: extracting a time-dependent capacitance value at one frequency selected from 100 Hz to 5 kHz using the frequency-dependent capacitance value at each measurement time obtained in step f). That is, integrity of the endothelial cell layer may be evaluated based on a change in the time-dependent capacitance value at one frequency.

More specifically, in the case in which a change in the capacitance is maintained within 5%, specifically 3%, more specifically 2% for a section from 6 to 36 hours after medium exchange, the endothelial cell may be evaluated as an endothelial cell layer without defect. In this case, the capacitance value at one frequency used for evaluation may be a capacitance value at an extremely low frequency of 100 to 300 Hz.

In the method for evaluating integrity of the endothelial cell layer according to the present invention, the medium exchanged at the time of medium exchange performed before step f) may further include a stimulation material biochemically and/or physically affecting the endothelial cell layer.

In this case, how the endothelial cell layer is affected by the stimulation material, that is, integrity of the endothelial cell layer according to the external stimulation material may also be evaluated. As the stimulation material, any biochemical, organic or inorganic material may be evaluated as long as an influence thereof on the endothelial cell layer should be evaluated. As a specific example, the stimulation material may include the drugs described in the method for screening drugs.

In the case in which the medium is exchanged with the medium containing the stimulation material, integrity of the endothelial cell layer according to the stimulation material may be evaluated by comparing a frequency-dependent capacitance value (hereinafter, integrity capacitance value) at each measurement time of a non-defective endothelial cell layer evaluated as non-defective and a frequency-dependent capacitance value (hereinafter, stimulation material capacitance value) at each measurement time of the endothelial cell layer contacting the stimulation material.

As a specific example, integrity of the endothelial cell layer according to the external stimulation material may be evaluated by assigning the capacitance (log scale) to a y axis and the frequency (log scale) to an x axis and line-fitting the frequency-dependent integrity capacitance value at each measurement time to obtain an alpha value (hereinafter, integrity alpha value), which is a slope, assigning the capacitance (log scale) to a y axis and the frequency (log scale) to an x axis and line-fitting the frequency-dependent stimulation material capacitance value at each measurement time to obtain an alpha value (hereinafter, stimulation material alpha value), which is a slope, and comparing the measurement time-dependent stimulation material alpha value and the integrity alpha value with each other.

More specifically, in the case in which an absolute value of a stimulation material alpha value after 25 to 60 hours of contact with the stimulation material is smaller than an absolute value of the integrity alpha value, the endothelial cell layer may be evaluated as an abnormal endothelial cell layer having a defect.

More specifically, when a slope of the alpha value, which is a change in a time-dependent stimulation material alpha value, has a different sign (+ or −) from that of a slope of the reference alpha value, which is a change in a time-dependent integrity alpha value, based on a stimulation material contact time point the endothelial cell layer may be evaluated as an abnormal endothelial cell layer having a defect.

As a specific example, after obtaining the alpha value (hereinafter, stimulation material alpha value), which is a slope, by assigning the capacitance (log scale) to a y axis and the frequency (log scale) to an x axis and line-fitting the frequency-dependent stimulation material capacitance value at each measurement time, in the case in which an absolute value of a time-dependent stimulation material alpha value is continuously decreased for at least 3 to 5 hours based on a stimulation material contact time point, the endothelial cell layer may be evaluated as an abnormal endothelial cell layer having a defect.

As a specific example, in the case in which a standardized stimulation material capacitance value obtained by dividing a stimulation material capacitance value at one frequency at a time point after 20 to 60 hours of the stimulation material contact time point by a stimulation material capacitance value at the stimulation material contact time point and the same frequency is smaller than a standardized integrity capacitance value obtained by dividing an integrity capacitance value at the same time point and the same frequency by an integrity capacitance value at the stimulation material contact time point and the same frequency, the endothelial cell layer may be evaluated as an abnormal endothelial cell layer having a defect.

As a specific example, in the case in which a standardized capacitance value obtained by dividing a capacitance value at one frequency selected from 100 Hz to 5 kHz at a time point after 10 to 30 hours of the stimulation material contact time point by an integrity capacitance value at the stimulation material contact time point and the same frequency is continuously decreased for at least 5 hours or more, the endothelial cell layer may be evaluated as an abnormal endothelial cell layer having a defect.

Here, one frequency may be an extremely low frequency of 100 to 300 Hz.

As described in specific examples, in the case in which paracellular permeability of the endothelial cell layer is abnormal, the endothelial cell layer may be evaluated as an abnormal endothelial cell layer having a defect. Therefore, a screening standard for drugs abnormally increasing paracellular permeability of the endothelial cell layer or adjusting abnormal permeability to normal permeability may be commonly used as a standard for evaluating integrity of an endothelial cell layer.

Therefore, specific examples of the method for evaluating integrity may have a standard equal or similar to the above-mentioned screening standards based on the method for screening drugs, the integrity capacitance value may correspond to the reference capacitance value, and the stimulation material capacitance value may correspond to the capacitance value (test capacitance value) of the endothelial cell layer contacting the drug. Therefore, specific examples of the method for evaluating integrity may include all of the contents suggested as screening standards as described above based on the method for screening drugs, and integrity may be evaluated with reference to the contents described above in the method for screening drugs.

As described above, the present applicant found that capacitance at a frequency region of 100 Hz to 5 kHz directly reflected paracellular permeability of the endothelial cell layer. Therefore, the present invention will be experimentally proven by measuring capacitance at a frequency region of 100 Hz to 5 kHz using brain vascular endothelial cells, deriving parameters to become standards for screening using the measured capacitance, and comparing results obtained by actually observing endothelial cell layers using immunocytochemistry.

Sensor

Gold (Au) electrodes 100 and 200 were manufactured on a glass substrate so as to have an entirely circular shape with a diameter of 7 mm but have an interdigitated structure as illustrated in FIG. 1. Heights (thicknesses) of two gold electrodes 100 and 200 were all 100 nm, and an interval between the electrodes was 30 μm, and a width of the gold electrode was 70 μm. A $SiO_2$ coating layer having a thickness of 50 nm was formed on the gold electrode. Then, an acrylic well 300 (Lab-Tek chamber slide, Lot no. 10118584) was attached for culturing cells so that the gold electrodes having the interdigitated structure were positioned in the wells. In this case, when the gold electrodes 100 and 200 having the interdigitated structure and the acrylic well 300 enclosing the gold electrodes on the glass substrate were considered as one unit sensor, 16 unit sensors spaced apart from each other were formed. All experiments were performed after sterilization was performed in an autoclave.

Cell bEND.3 (American Type Culture Collection, USA), which is a mouse brain vascular endothelial cell line, was used. As a cell culture medium, DMEM (Dulbecco's Modified Eagle Medium, Gibco) in which 10 vol % fetal bovine serum (FBS, Gibco) and 1 vol % penicillin-streptomycin (Gibco) were mixed was used. Cells were cultured at a temperature of 37° C. under atmosphere of 95 vol % air and 5 vol % $CO_2$ for 24 hours.

Stabilization of Cell Layer

Endothelial cells ($1 \times 10^5$/well) and the culture medium (DMEM with 10 vol % FBS and 1 vol % penicillin-streptomycin) were seeded in each of the 16 wells. Next, the cells were cultured at a temperature of 37° C. under atmosphere of 95 vol % air and 5 vol % $CO_2$.

Medium Exchange

After the cells were cultured for stabilization for 24 hours, the culture medium was exchanged.

A reference culture medium composed of DMEM (Dulbecco's Modified Eagle Medium, Gibco) containing 1 vol % penicillin-streptomycin was used as a culture medium of a control group, a reference culture medium containing mouse vascular endothelial growth factor-165 (VEGF-165, Cell signaling, 20 ng/ml) was used as a culture medium of a first drug treatment group, a reference culture medium containing VEGF-165 (20 ng/ml) and bevacizumab (Genentech, 0.3 mg/ml) was used as a culture medium of a second drug treatment group, and a reference culture medium containing bevacizumab (Genentech, 0.3 mg/ml) was used as a culture medium of a third drug treatment group.

Measurement of Capacitance

The sensor was disposed in an incubator in which the temperature of 37° C. and the atmosphere of 95 vol % air and 5 vol % $CO_2$ were maintained, and connected to a data collecting device collecting data from the sensor.

In order to confirm whether or not stabilization was normally performed in each sensor, capacitance was measured from a time point (t=0) at which the cultured endothelial cells were seeded in the well for stabilizing a cell layer.

Capacitance was measured with an AC voltage of 10 mV while changing a frequency from 100 Hz to 100 kHz using a precision impedance analyzer (Cat. No. 4294A, Agilent). Measurement was performed in each unit sensor every 5 minutes, and measurement values were collected using a data logger (data acquisition switch unit, cat. no. 34970A, Agilent) connected to the precision impedance analyzer.

Western Blot Analysis

The same amount of proteins extracted from bEND.3 cells treated with VEGF-165 (20 ng/ml), bEND.3 cells treated with bevacizumab (0.3 mg/ml), or bEND.3 cells treated with VEGF-165 (20 ng/ml) and bevacizumab (0.3 mg/ml) were separated by Sodiumdodecylsulfate-polyacrylamide gel electrophoresis (SDS-PAGE), and then transferred to a nitrocellulose membrane. Thereafter, the membrane was cultured together with primary antibodies. As the primary antibodies, zona occludens-1 (ZO-1, Invitrogen) and anti-β-actin (Sigma-Aldrich) were used. Next, the membrane was cultured together with species-specific and peroxidase-conjugated secondary antibodies (Thermo) for 1 hour. The visualization of bands was performed with ECL solution (Daeillab) and ImageQuant LAS4000 system (GE).

Immunocytochemistry

After measurement of capacitance was completely terminated, the culture medium was removed from each well. Then, the cells remaining in the sensor were fixed using phosphate buffer saline (PBS) containing 4 wt % of paraformaldehyde (PFA) at room temperature for 15 minutes.

Permeabilization of cells was performed with PBS containing 0.1 wt % Triton X-100.

Then, in order to prevent non-specific binding, PBS containing 3 wt % bovine serum albumin (BSA) was applied and treated onto cells at room temperature for 60 minutes.

Next, after treating cells with antibodies against ZO-1 (cat. no. 339194, Invitrogen) or claudin-5 (cat. no. 352588, Invitrogen) overnight at 4° C., nuclear staining was performed with 4',6-diamidino-2-phenylindole (DAPI) at room temperature for 15 minutes. Thereafter, cells were observed using the confocal microscope after fixing the cells using a mounting solution.

Statistical Analysis

Differences between control and drug treatment groups were evaluated using 2-tailed unpaired Student's T-test. All statistical analyses were performed using Program. P-values which were less than 0.05 were considered to be statistically significant. Standard error of the mean (SEM) in addition to the mean were also illustrated in the accompanying drawings.

Figure 2A:
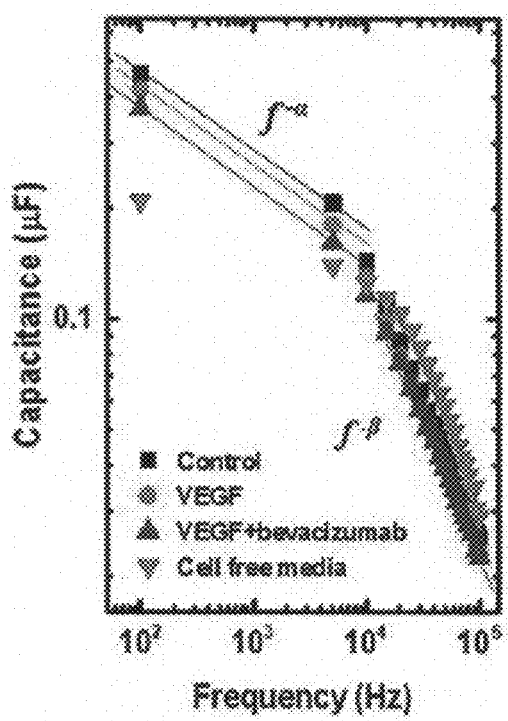
FIG. 2A and FIG. 2B are views illustrating a frequency-dependent capacitance value of an endothelial cell layer in the method for screening drugs according to the exemplary embodiment of the present invention.
Figure 2B:
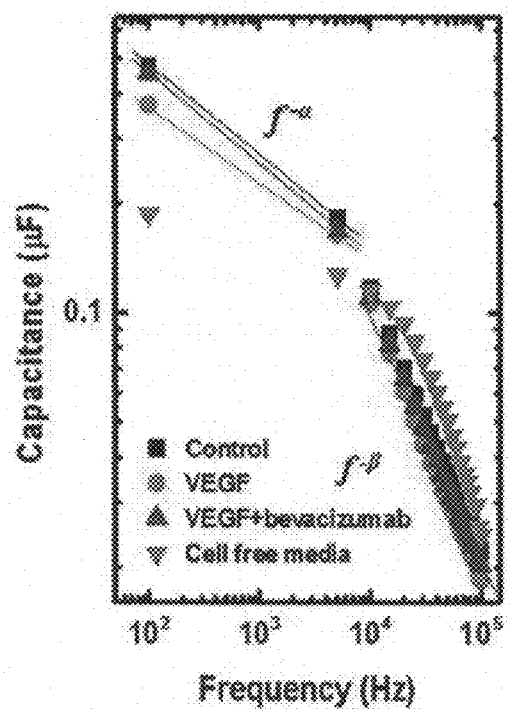

FIGS. 2A and 2B are views illustrating frequency-dependent capacitance values of control group (represented by 'control' in the accompanying drawings), the first drug treatment group (represented by 'VEGF' in the accompanying drawings), the second drug treatment group (represented by 'VEGF+bevacizumab' in the accompanying drawings), and culture media itself (represented by 'cell free media' in the accompanying drawings) in which cells did not exist. FIG. 2A is a view illustrating results at a time point (t=16 h) at which stabilization was performed, and FIG. 2B is a view illustrating results at a time point (t=60 h) after 36 hours of medium exchange. In this case, FIGS. 2A and 2B are views (log-log scale) in which capacitance was assigned to a y axis and the frequency was assigned to an x axis, and capacitance of the cell in which only the culture medium was seeded without cells was also represented by 'cell free media' and illustrated as reference.

As illustrated in FIGS. 2A and 2B, it was observed that as the frequency was increased, capacitance was decreased. A beta value, which is a slope between several kHz to several ten MHz, particularly, a beta value at 75 kHz or more did not have a significant difference in time- and frequency-dependent capacitance according with or without drug treatment and the kind of drugs, but an alpha value, which is a slope between 100 Hz to 5 kHz, has a significant difference in time- and frequency-dependent capacitance according with or without drug treatment and the kind of drugs.

Figure 3A:
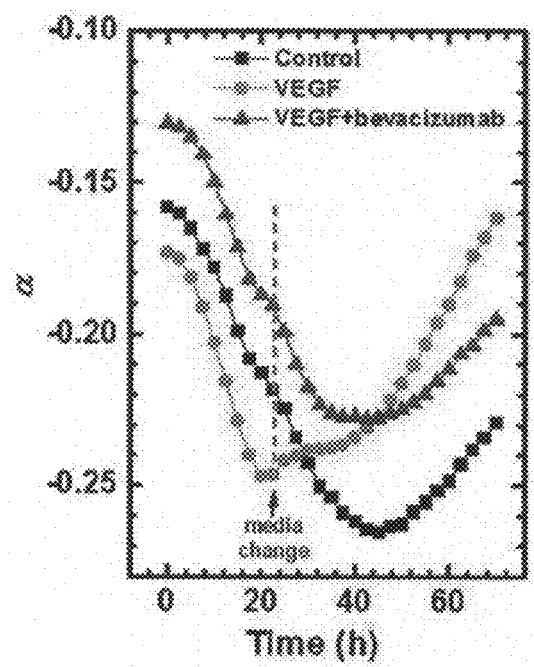
FIG. 3A and FIG. 3B are views showing measurement time-dependent alpha and beta values in the method for screening drugs according to the exemplary embodiment of the present invention.
Figure 3B:
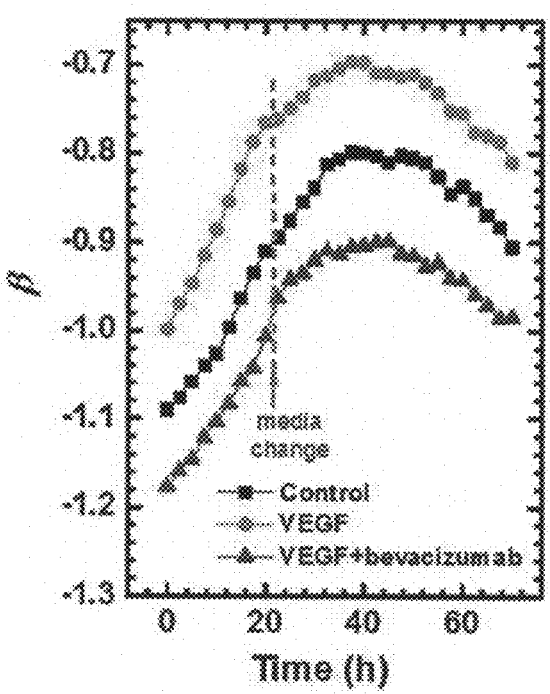

FIGS. 3A and 3B are views (log-log scale) in which capacitance was assigned to a y axis and the frequency was assigned to an x axis, wherein FIG. 3A is a view illustrating an alpha value, which is a slope between 100 Hz to 5 kHz, and FIG. 3B is a view illustrating a beta value, which is a slope between several kHz to several ten MHz, according to the measurement time. In this case, as medium exchange was performed after the cells were stabilized for 24 hours, t=24 h becomes a drug contact time point, which was represented by a dotted line and 'media change' in the accompanying drawings.

FIGS. 3A and 3B are views illustrating time-dependent change in the alpha and beta values according to the treatment group. As illustrated in FIG. 3B, even after medium exchange was performed, there was no significant time-dependent change in the beta value. In detail, with the passage of time, there was a similar tendency that the beta value was gradually increased but had a flat plateau region at 44 hours (t=44 h), and then, gradually decreased.

However, as illustrated in FIG. 3A, in the case of the first drug treatment group, immediately after medium exchange, a change in the alpha value was different from that of the control group. More specifically, in the case of the first drug treatment group, a gradual increase in the alpha value was observed, but in the cases of the control group and the second drug treatment group, after about 20 hours of medium exchange (t=44 h), the alpha value was lowest.

Further, in the cases of the second drug treatment group and the control group, a change in the time-dependent alpha value was not generated by medium exchange, but in the case of the first drug treatment group, a tendency was clearly changed from a tendency that a change in the time-dependent alpha value was decreased to a tendency that the change in the time-dependent alpha value was increased by medium exchange. That is, in the cases of the second drug treatment group and the control group, a slope of the alpha value, which is the change in the time-dependent alpha value, had a negative (−) value based on the drug contact time point, but in the case of the first drug treatment group, it may be appreciated that a negative (−) slope before contact with the drug was changed into a positive (+) slope after contact with the drug, such that a sign itself of the slope was changed. In this case, since the alpha value itself was a negative value, the alpha value was increased, which means that an absolute value of the alpha value was decreased based on the absolute value of the alpha value.

Figure 4A:
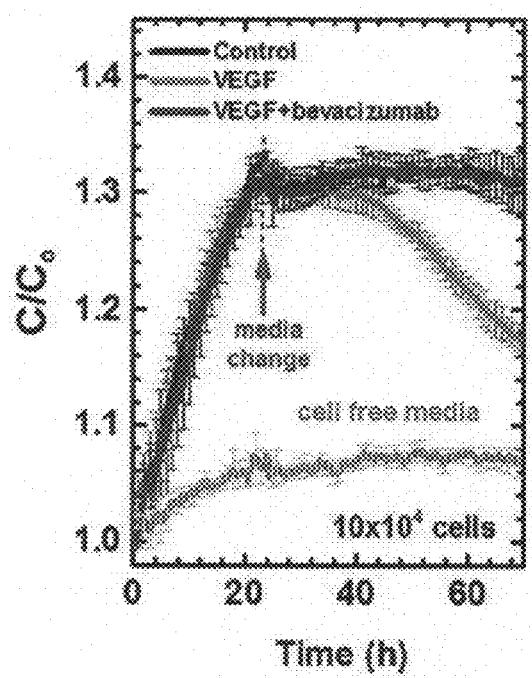
FIG. 4A and FIG. 4B are views illustrating a measurement time-dependent capacitance value at a frequency of 100 Hz in the method for screening drugs according to the exemplary embodiment of the present invention.
Figure 4B:
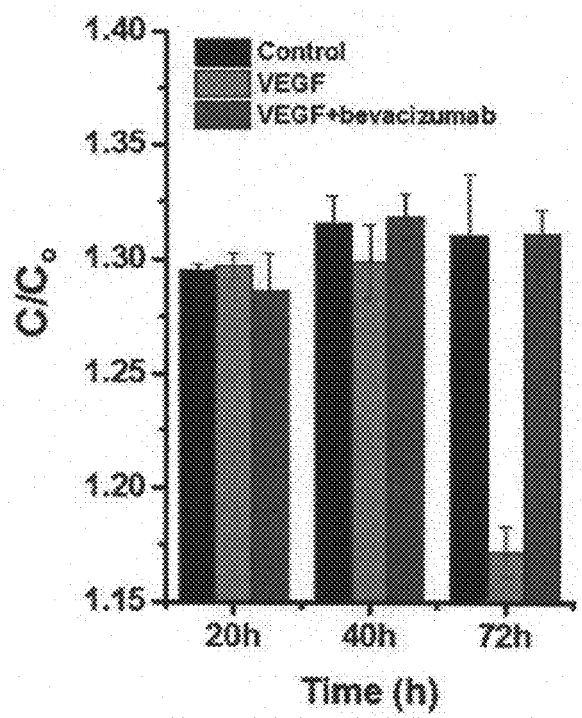

FIGS. 4A and 4B are views illustrating a time-dependent capacitance value at a frequency of 100 Hz. In this case, the capacitance value was standardized by dividing the capacitance value by a capacitance value ($C_0$) measured at a time point (t=0) at which the cells were injected into the well (stabilization was initiated). Here, in an example of FIGS. 4A and 4B, since measurement of capacitance was performed at a stabilization process in order to also observe a change in the capacitance value in the stabilization process, standardization was performed using the capacitance value at the time point at which stabilization was initiated, but substantially, standardization may be performed using a capacitance value at the drug contact time point.

As a result of observing the time-dependent capacitance value at the extremely low frequency (100 Hz) and a change tendency thereof, in the control group and the second drug treatment group, there was no significant difference before and after the drug treatment. However, in the case of the first drug treatment group, a difference that was clearly different from other groups was observed. In the case of the first drug treatment group, the capacitance value at the extremely low frequency was clearly decreased from a time point (t=44 h) after 20 hours of medium exchange, and rapidly decreased from a time point (t=48 h) after 24 hours of medium exchange. Particularly, a P-value at the time point of 48 hours (t=72 h) after medium exchange was 0.01, such that the time point (t=72 h) may be used as a statistically significant and clear standard.

Figure 5A:
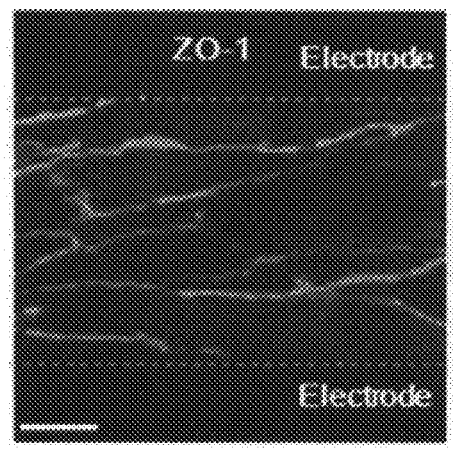
FIG. 5A to FIG. 5I are photographs of tissue observed by staining endothelial cell layers fixed between two electrodes using immunocytochemistry after measurement of capacitance was completed.
Figure 5B:
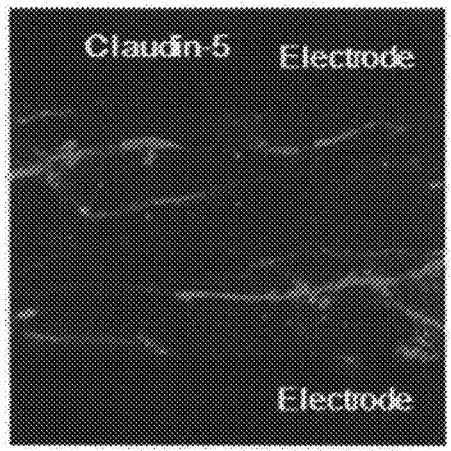
Figure 5C:
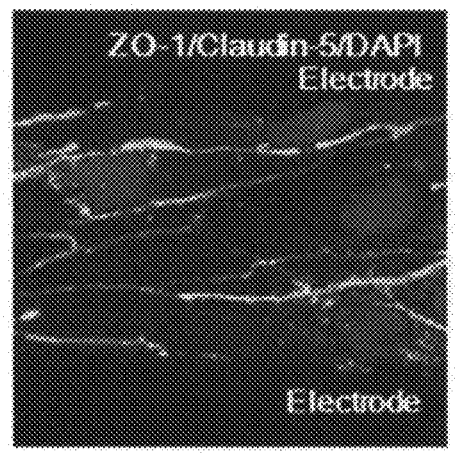
Figure 5D:
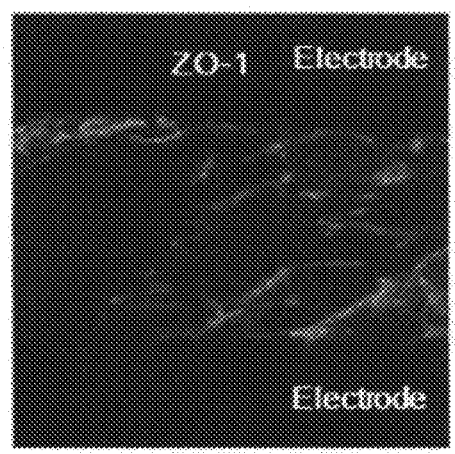
Figure 5E:
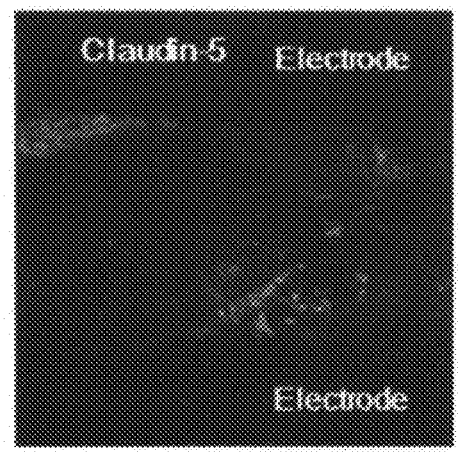
Figure 5F:
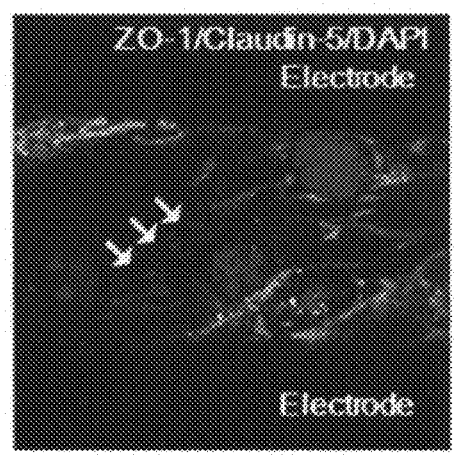
Figure 5G:
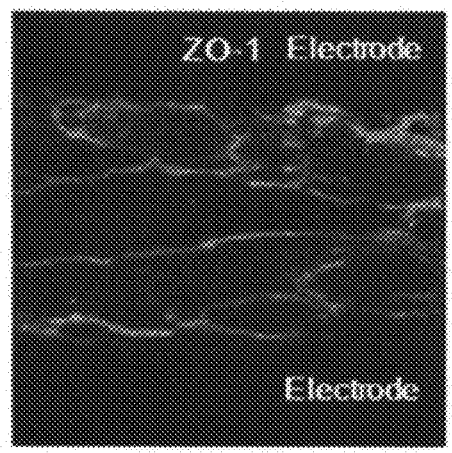
Figure 5H:
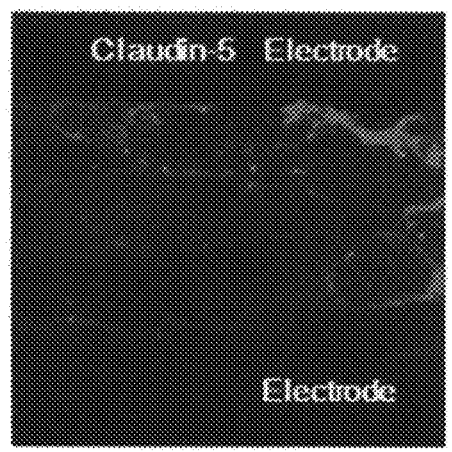
Figure 5I:
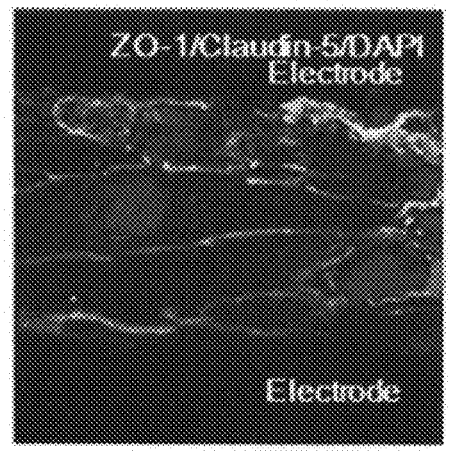

FIGS. 5A to 5I are photographs showing tissue observed by fluorescent staining endothelial cell layers fixed between two electrodes using Immunocytochemistry after measurement of capacitance was completed. In detail, FIGS. 5A to 5C illustrate results of the control group, FIGS. 5D to 5F illustrate results of the first drug treatment group, and FIGS. 5G to 5I illustrate results of the second drug treatment group. Here, all drawings illustrated in FIGS. 5A to 5I are photographs measured at the same magnification, and a scale bar of FIG. 5A is 10 μm. In each drawing, upper and lower black portions are electrodes, and represented by 'electrode' in the drawings. Further, materials used in florescent staining, ZO-1, Claudin-5, or ZO-1/Claudin-5/DAPI (samples stained with ZO-1, Claudin-5, and DAPI), were also represented in each drawing.

As illustrated in photographs of FIGS. 5A to 5I, it may be appreciated that in the case of the first drug treatment group, alignment of tight junction proteins was disturbed as represented by an arrow of FIG. 5F, and in the cases of the control group and second drug treatment groups, alignment of the tight junction proteins was not disturbed unlike the first drug treatment group.

Figure 6:
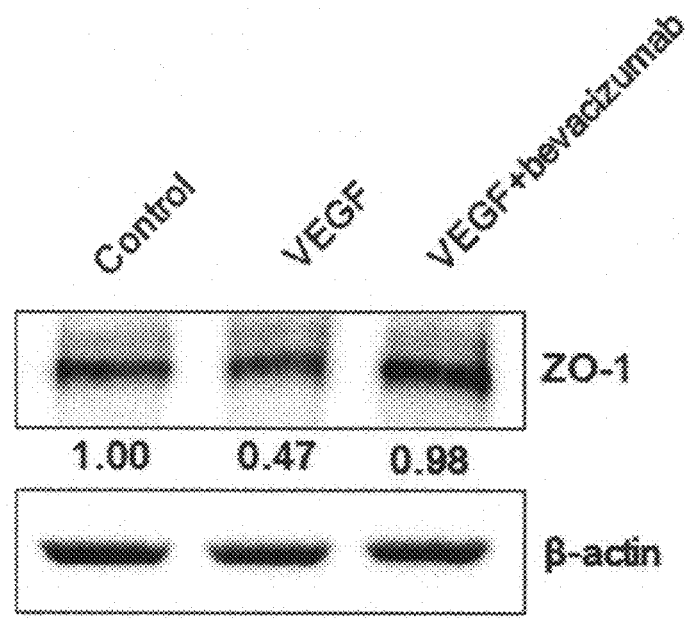
FIG. 6 is view illustrating western blot results of the endothelial cell layer used in measurement after measurement of capacitance was completed.

FIGS. 6A and 6B are views illustrating western blot results of the control group, the first drug treatment group, and the second drug treatment group. As illustrated in FIGS. 6A and 6B, it may be appreciated that in the case of the first drug treatment group, down regulation of the tight junction proteins was generated, but in the cases of the second drug treatment group and the control group, down regulation was not generated. Numerical values illustrated in FIGS. 6A and 6B mean amounts of proteins in bands, and it may be appreciated that in the cases of the control group and the second drug treatment group, numerical values were similar to each other, but in the case of the first drug treatment group, the numerical values were decreased.

Stabilization (fixation) of a normal endothelial cell layer may be verified by confirming whether or not a time-dependent capacitance value at an extremely low frequency was stably constantly maintained.

An abnormally sparse endothelial cell layer was fixed between electrodes at the time of stabilization using secondary culturing for 24 hours by intentionally seeding (coverage: 50%) and culturing endothelial cells between the electrodes of the sensor so that a concentration of the cells was sparse. In detail, at the time of stabilization (fixation), endothelial cells ($5 \times 10^4$/well) and a culture medium (DMEM, 10 wt % FBS, 1 wt % penicillin-streptomycin) were seeded in each of the 16 wells and then cultured at a temperature of 37° C. under atmosphere of 95 vol % air and 5 vol % $CO_2$ for 24 hours. Thereafter, medium exchange was performed using a reference culture medium (DMEM containing 1 vol % penicillin-streptomycin) similarly to the control group.

Figure 7A:
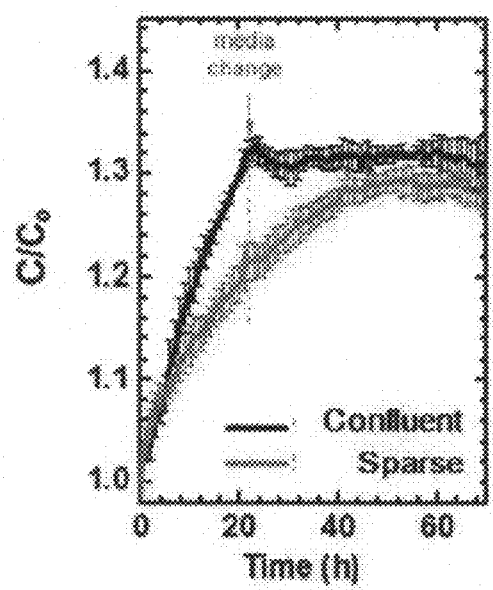
FIG. 7A and FIG. 7B are views illustrating a measurement time-dependent capacitance value at a frequency of 100 Hz and an optical photograph while changing the status of a stabilized endothelial cell layer in the method for screening drugs according to the exemplary embodiment of the present invention.
Figure 7B:
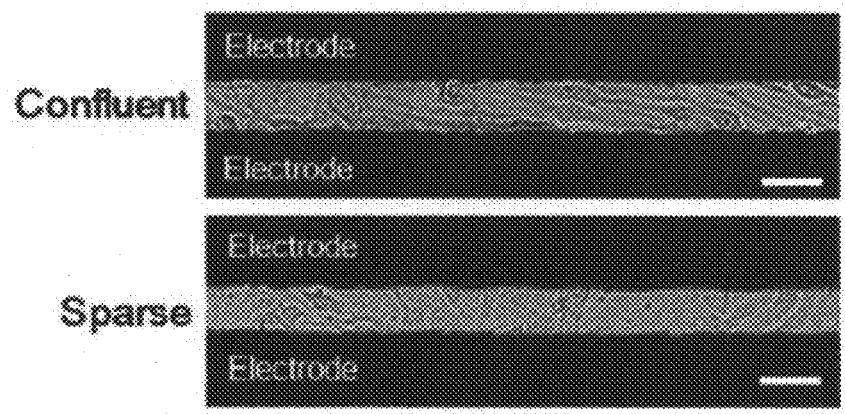

FIG. 7A is a view illustrating a time-dependent standardized capacitance value at 100 Hz of a normal endothelial cell layer fixed between two electrodes (represented by 'confluent' in FIGS. 7A and 7B) and an abnormal endothelial cell layer fixed between two electrodes (represented by 'sparse' in FIGS. 7A and 7B), and FIG. 7B is an optical microscope photograph obtained by observing the endothelial cell layers fixed between two electrodes.

As illustrated in FIGS. 7A and 7B, it may be appreciated that in the case of the normal endothelial cell layer, constant capacitance was stably maintained after medium exchange, but in the case of the abnormal endothelial cell layer having a sparse cell density, capacitance was not maintained but was increased. In detail, it may be appreciated that in the case of the normal endothelial cell layer, a change in the capacitance value was maintained within 1.5% in a section from a time point (t=30 h) after 6 hours of medium exchange to a time point (t=60 h) after 36 hours. On the other hand, it may be appreciated that in the case of the abnormal endothelial cell layer having a sparse cell density, the capacitance was not stably maintained but was gradually increased. Therefore, it may be appreciated that evaluation (verification) of the endothelial cell layer itself may be performed through the change in the time-dependent capacitance at an extremely low frequency.

It may be appreciated through the above-mentioned measurement results of capacitance and verification using Immunocytochemistry and western blot analysis that capacitance of the endothelial cell layer at a frequency region of 100 Hz to 5 kHz was a factor directly reflecting paracellular permeability of the endothelial cell layer, and drugs affecting paracellular permeability may be screened through a change in the time-dependent capacitance at an extremely low frequency and/or a change in the time-dependent alpha value by measuring time- and frequency-dependent capacitance.

In the method for screening drugs or method for evaluating integrity as described above, as the detailed standard for screening or evaluation, a difference between the reference alpha value and the measured alpha value, a difference of the change tendency in the time-dependent alpha value, a difference between the reference capacitance value and the measured capacitance value at one frequency, a difference of the change tendency in the time-dependent capacitance value, the change tendency in the measured alpha value itself, the change tendency in the measured capacitance value itself, and the like, were suggested. Screening or evaluation may be performed using at least one standard of the detailed standards suggested for screening or evaluation, and evaluation may be independently performed according to each standard using two or more detailed standards. In this case, reliability of screening or evaluation may be improved using two or more detailed standards.

Hereinafter, a blind test was performed by exchanging a medium in a state in which a drug contained in the medium was not known at the time of medium exchange, screening drugs affecting permeability of an endothelial cell layer according to the exemplary embodiment of the present invention, and then comparing screening results in each well and drugs contained in the exchanged medium in each well.

Blind Test

After culturing ARPE-19 (retinal pigmented epithelium, American Type Culture Collection (ATCC), ATCC® CRL-2302™), which is human retinal epithelial cells, instead of bEND.3 similarly to the case of using bEND.3, the cultured ARPE-19 was seeded in the same sensor as that used at the time of measuring bEND.3 so that coverage was 100%. Then, stabilization (fixation) was performed under the same conditions and time as those at the time of stabilizing bEND.3.

After the cells were cultured for stabilization for 24 hours, the culture medium was exchanged.

As the exchanged medium, a reference culture medium containing tumor necrosis factor-alpha (TNF-α, R&D system, 210-TA-020/CF, 10 ng/ml) or a reference culture medium containing tumor necrosis factor-alpha (TNF-α, R&D system, 210-TA-020/CF 10 ng/ml) and TNF-α antibody (Human TNF-alpha MAb, R&D system, MAB610, 2 μg/ml) was prepared. In this case, as the reference culture medium, DMEM:F12 containing 1 vol % penicillin-streptomycin (Gibco) was used similarly to the case of using bEND.3.

After stabilization was performed, medium exchange was randomly performed on each well using the prepared culture media. In this case, medium exchange was performed on a well (reference sample) at a predetermined position using a pure reference culture medium not containing TNF-α or TNF-α antibody, such that a frequency-dependent reference capacitance value at each measurement time was also simultaneously obtained.

Capacitance was measured under the same conditions and the same time interval as those in the case of using bEND.3.

After measurement was performed, in each well, in the case in which an absolute value of an alpha value at a time point (t=50 h based on stabilization) after 26 hours of medium exchange is smaller than an absolute value of a reference alpha value at the same time point, the drug was screened as a drug increasing paracellular permeability.

Independently, in each well, when a standardized capacitance value was compared with a standardized reference capacitance value at a time point (t=72 h based on stabilization) after 48 hours of medium exchange, in the case in which the standardized capacitance value was 95% or less, which is small, of the standardized reference capacitance value, the drug was screened as a drug increasing paracellular permeability.

Independently, in each well, in the case in which a standardized capacitance value at 100 Hz was continuously decreased for 5 hours or more at a time point (t=34 h based on stabilization) after 10 hours of medium exchange, the drug was screened as a drug increasing paracellular permeability.

As screening results, all wells (samples) screened as wells contacting drugs increasing paracellular permeability were wells of which the medium was exchanged with medium containing only TNF-α, and it was confirmed that all wells of which the medium was exchanged with the medium containing only TNF-α were screened as wells contacting the drug increasing paracellular permeability.

In the screening using a difference between the reference alpha value and the measured alpha value, in the screening using a difference between the reference capacitance and the measured capacitance, and in the screening using a time-dependent change tendency in the measured capacitance, all the same screening results were obtained.

Figure 8:
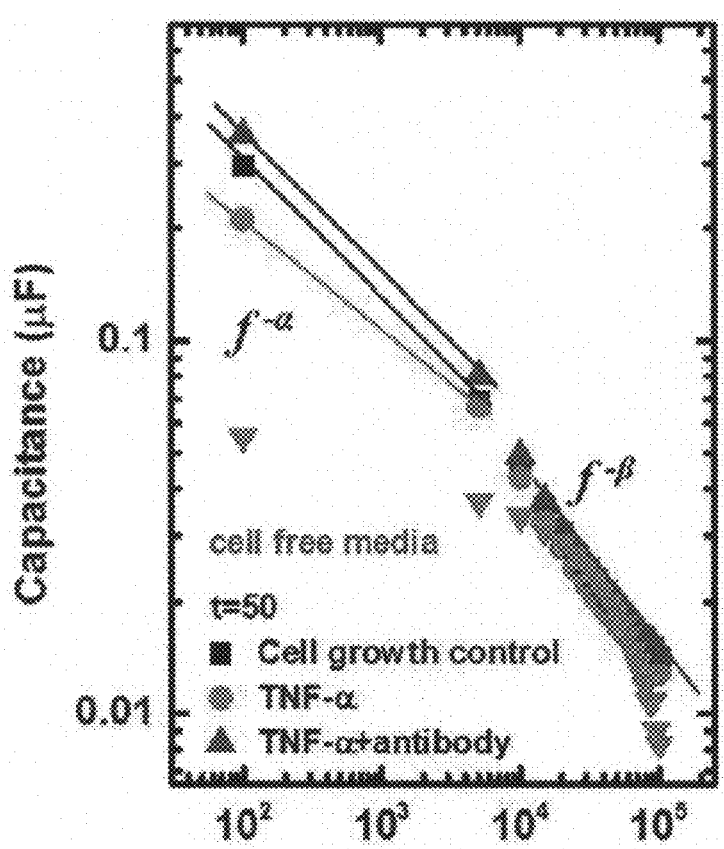
FIG. 8 is a view showing measurement time-dependent alpha and beta values in the method for screening drugs according to the exemplary embodiment of the present invention.

As a specific example of the screening, FIG. 8, which illustrates a result used in the blind test, is a log-log plot graph illustrating the measured capacitance value at each frequency and the frequency at a time point (t=50 h based on a time point at which cells were seeded in the wells) after 26 hours after medium exchange. In FIG. 8, a graph represented by a black tetragon illustrates results of the reference sample, a graph represented by a red circle illustrates results of the sample screened as a sample contacting a drug increasing paracellular permeability.

As another specific example of the screening, after performing standardiziation using capacitance at 100 Hz measured at a time point at which stabilization was initiated, a standardized reference capacitance value of a reference sample at a time point (t=72 h based on stabilization) after 48 hours of medium exchange was 1.44, and a standardized capacitance value of a sample screened as a sample contacting a drug increasing paracellular permeability was 1.31.

As another specific example of the screening, in a sample screened as a sample contacting a drug, after performing standardization using capacitance at 100 Hz measured at a time point at which stabilization was initiated, a standardized capacitance value was continuously decreased for 48 hours based on a time point (t=34 h based on stabilization) after 10 hours of medium exchange.

Figure 9A:
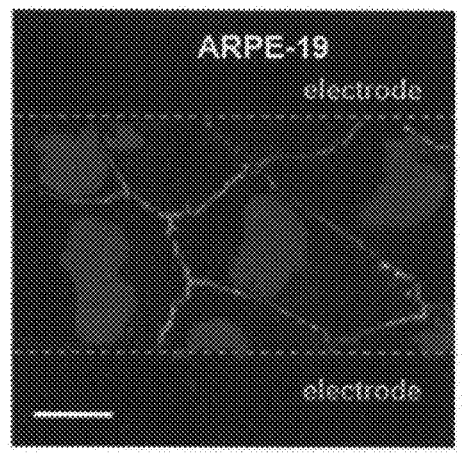
FIG. 9A to FIG. 9C are photographs of tissue observed by fluorescent staining endothelial cell layers fixed between two electrodes using immunocytochemistry after measurement of capacitance was completed.

After performing the screening, as described above, fluorescent staining (using ZO-1 and DAPI) was performed on the endothelial cell layer fixed between two electrodes using immunocytochemistry, and then the endothelial cell layer was observed. FIG. 9A illustrates results of the reference sample, FIG. 9B illustrates results of the sample of which the medium was exchanged with the medium containing TNF-α, and FIG. 9C illustrates results of the sample of which the medium was exchanged with the medium containing both of TNF-α and TNF-α antibody.

Figure 9B:
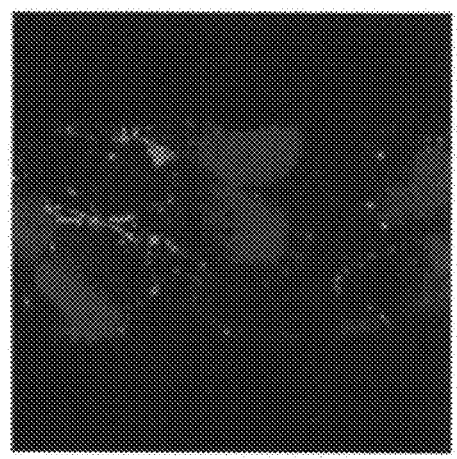
Figure 9C:
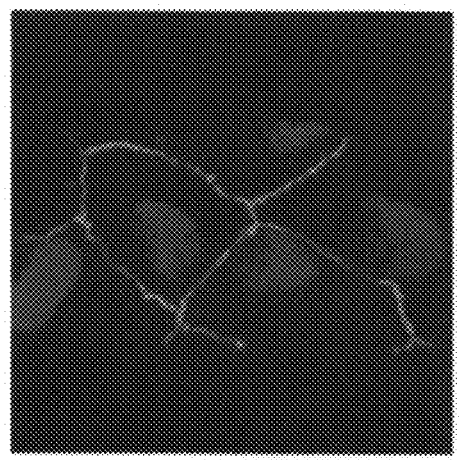

It may be appreciated from FIGS. 9A to 9C that alignment of tight junction proteins was disturbed only in the sample of which the medium was exchanged with the medium containing TNF-α, which coincided with the results of the blind test as described above.

The present invention provides a method capable of measuring and evaluating intercellular binding state (intercellular structure) of the 'endothelial cell layer' against external stimulation materials including drugs in vitro through a significantly simple sensor capable of measuring frequency-dependent capacitance, based on the founding that the time- and frequency-dependent capacitance of the endothelial cell layer directly reflects paracellular permeability of the endothelial cell layer.

Therefore, the present invention may provide a method capable of testing an influence of the external stimulation material on the paracellular permeability of the endothelial cell layer, and provide a method for screening drugs capable of screening drugs affecting paracellular permeability of the endothelial cell layer.

The method for screening drugs according to the present invention may simply and rapidly screen drugs affecting paracellular permeability of the endothelial cell layer in vitro regardless of the kind of drugs using a cheap device.

Further, in the method for screening drugs according to the present invention, the screening of drugs is performed only based on the time- and frequency-dependent capacitance of the endothelial cell layer, such that at the time of screening drugs, there is no need for a highly professional knowledge associated with a pharmacological field or medical field.

In addition, the method for screening drugs according to the present invention may provide standards for interaction between drugs, minimum doses of drugs, or the like, that should be previously known in order to substantially obtain an effect to be expected at the time of actually using drugs, for example, in the case in which two or more different drugs are combined, in the case in which a composition is changed in the same combination, or the like, in addition to the case of using a single drug.

Independently of the above-mentioned method for screening drugs, the present invention may provide a method capable of judging whether the endothelial cell layer has normal paracellular permeability, or has abnormal paracellular permeability, such that integrity of the endothelial cell layer may be measured and evaluated.

Further, the present invention may provide a method for measuring basic paracellular permeability of the endothelial cell layer in order to conduct basic research such as research into mechanisms of various diseases caused by or causing abnormal permeability of the endothelial cell layer.

Hereinabove, although the present invention is described by specific matters, exemplary embodiments, and drawings, they are provided only for assisting in the entire understanding of the present invention. Therefore, the present invention is not limited to the exemplary embodiments. Various modifications and changes may be made by those skilled in the art to which the present invention pertains from this description.

Therefore, the spirit of the present invention should not be limited to the above-described embodiments, and the following claims as well as all modified equally or equivalently to the claims are intended to fall within the scope and spirit of the invention.

What is claimed is:

1. A method for screening drugs, comprising:
   a) fixing a cultured endothelial cell layer between first and second electrodes spaced apart from each other and facing each other;
   b) contacting the fixed endothelial cell layer with a drug;
   c) measuring capacitance of the endothelial cell layer contacting the drug at a plurality of measurement times while changing the frequency in a range of 100 Hz to 5 kHz to obtain a frequency-dependent capacitance value at each measurement time; and
   d) determining whether the drug affects paracellular permeability of the endothelial cell layer based on a difference in an increasing rate or a decreasing rate of the frequency-dependent capacitance value at each measurement time,
   wherein step a) is performed in a well attached to enclose a region in which the first and second electrodes spaced apart from each other and facing each other are formed,
   wherein both the first and second electrodes are formed on a single substrate, and the first and second electrodes have a same height, and
   wherein capacitance in step c) is measured by applying an AC voltage of 5 to 15 mV to the first and second electrodes.

2. The method for screening drugs of claim 1, further comprising, after step a), measuring capacitance of a fixed endothelial cell layer that does not contact the drug at a plurality of measurement times while changing the frequency in a range of 100 Hz to 5 kHz to obtain a frequency-dependent reference capacitance value at each measurement time.

3. The method for screening drugs of claim 1, wherein the frequency is in a range of 100 to 300 Hz.

4. The method for screening drugs of claim 1, wherein the endothelial cell layer is a vascular endothelial cell layer.

5. The method for screening drugs of claim 4, wherein the vascular endothelial cell layer is a brain microvascular endothelial cell layer.

6. The method for screening drugs of claim 1, wherein in step a), a coverage is at least 95%, based on the coverage which is a ratio (Ac/Ao*100) of an area (Ac) of a lower portion of the well covered by cultured endothelial cells to the area (Ao) of the lower portion of the well.

* * * * *